United States Patent [19]

Bauer, Jr. et al.

[11] Patent Number: 5,488,141
[45] Date of Patent: Jan. 30, 1996

[54] REMOVAL OF CARBONYL IMPURITIES FROM αβ UNSATURATED CARBOXYLIC ACID ESTERS

[75] Inventors: William Bauer, Jr., Huntingdon Valley; Nelson I. Quiros, Telford; Rita K. Upmacis, North Wales, all of Pa.

[73] Assignee: Rohm and Haas Company, Philadelphia, Pa.

[21] Appl. No.: 258,011

[22] Filed: Jun. 10, 1994

[51] Int. Cl.$^6$ .................................................. C07C 69/74
[52] U.S. Cl. ............................................................. 560/218
[58] Field of Search ............................................. 560/218

[56] References Cited

FOREIGN PATENT DOCUMENTS 102642 3/1984 European Pat. Off. .
62-45222 9/1987 Japan .

OTHER PUBLICATIONS

CA 106:120360 1985.

Primary Examiner—Paul J. Killos
Attorney, Agent, or Firm—Thomas D. Rogerson; Richard A. Haggard

[57] ABSTRACT

This invention is a method for removing certain carbonyl containing impurities from α,β-unsaturated carboxylic acid ester with an aqueous solution of a bisulfite or dithionite salt.

12 Claims, No Drawings

5,488,141

REMOVAL OF CARBONYL IMPURITIES FROM α β UNSATURATED CARBOXYLIC ACID ESTERS

BACKGROUND OF THE INVENTION

This invention relates to a method of removing aldehyde impurities from α,β-unsaturated carboxylic acid esters, such as acrylate esters and methacrylate esters (hereinafter "(meth)acrylate esters"). Processes for producing such esters which incorporate oxidative steps, such as the vapor phase oxidation of propylene, isobutylene, tertiary butanol, methacrolein, acrolein, or isobutyraldehyde to afford acrylic or methacrylic acid (hereinafter (meth)acrylic acid) followed by esterification to a (meth)acrylate ester, are known to result in product mixtures which contain quantities of aldehyde and other carbonyl containing impurities, such as benzaldehyde, furfural, protoanemonin, methacrolein, and acrolein. These impurities are undesirable because they may react with the (meth)acrylate esters in subsequent reactions, they may interact with other reactants which are intended to react with the (meth)acrylate esters in subsequent reactions, they may react to form colored impurities, or they may directly inhibit subsequent reactions. In addition, these materials may interfere with subsequent purification of the (meth)acrylate, whether at the acid or ester stage. For these reasons it is highly desirable to remove these impurities from the (meth)acrylate esters.

The use of bisulfites for removal of aldehydes and protoanemonin from methacrylic and acrylic acids is known. See for example, Japanese Patent No. 62-45222B and European Patent No. 0 102 642 A1 which disclose processes for purifying methacrylic acid with an aqueous bisulfite solution. These processes require several distillation steps to remove high and low boiling materials. In addition, these methods all require aqueous solutions of both the acrylic and methacrylic acid and the bisulfite with the resulting disposal and recycling problems. Thus, it is known that bisulfites are useful for removing carbonyl containing impurities, especially aldehydes and protoanemonin, from (meth)acrylic acids. The bisulfite acts by reacting with the carbonyl group to form the corresponding sulfonate ester salt. Such salts are water soluble and are easily separated from (meth)acrylic acid by use of solvent/solvent extraction using a water immiscible organic solvent. However, these methods all require the use of water-immiscible solvents to allow extraction of the carbonyl containing impurities into an aqueous phase. The aqueous phase is then separated from the acid. Solvent removal is then necessary for further purification.

We have discovered that carbonyl containing impurities can be removed from esters of α,β-unsaturated carboxylic acids by extraction with bisulfite under neutral conditions rather than under the previously known acid conditions. As a result, treating esters on an industrial scale may be more cost effective than treating acids. Advantages of this invention are that the use of solvents is reduced or eliminated and unconsumed bisulfite may be easily recycled. Elimination of the solvent simplifies the purification process and reduces undesirable organic waste generation.

SUMMARY OF THE INVENTION

This invention provides a method for removing a variety of carbonyl containing impurities from esters or mixtures of esters of α,β-unsaturated carboxylic acids. This is accomplished by thoroughly mixing an aqueous solution of a bisulfite or dithionite salt with the ester, which may be dissolved in a water-immiscible solvent, allowing the mixture to separate into an aqueous and an organic layer, and separating the ester containing organic layer. The terms "thoroughly mixed" and "effectively admixed" define a mixing of the aqueous and organic layers that is sufficiently intimate such that, after separation of the layers, the quantity of carbonyl containing impurities in the organic layer is reduced to a desired level. The terms "esters" or "ester" includes mixtures of esters. Although not necessary, the ester may be isolated from the water immiscible solvent, if such a solvent is used, by any one of a number of techniques familiar to those skilled in the art such as dehydration followed by distillation or solvent evaporation.

DETAILED DESCRIPTION OF THE INVENTION

α,β-Unsaturated carboxylic acid esters which can be purified using this invention include those produced by esterification of $C_3$–$C_{10}$ α,β-unsaturated carboxylic acids, such as acrylic, methacrylic, 2-butenoic, cyclohexenoic, maleic, itaconic, and the like, with $C_1$–$C_{10}$ alcohols such as methanol, ethanol, normal and iso-propanol, the primary, secondary, and tertiary butanols, cyclohexanol, octanol, ethyl hexanol, glycols, decanol and the like. Preferred esters are those prepared from $C_3$–$C_5$ carboxylic acids and $C_1$–$C_5$ alcohols; more preferred are methyl acrylate, butyl acrylate, ethyl acrylate, butyl methacrylate, and methyl methacrylate; most preferred are butyl acrylate and ethyl acrylate because of their commercial importance.

Although the invention is more appropriate for use when the carboxylic acid reactant is produced via an oxidative route, such as front catalytic oxidation to produce (meth)acrylic acid, because such synthesis routes also produce aldehyde containing impurities, the procedure may also be used whenever it is desired to remove carbonyl containing impurities which will react with bisulfites or dithionites to form water soluble sulfonate ester salts. Members of this group of impurities, which are particularly difficult to remove from esters, include benzaldehyde, furfural, and protoanemonin.

The ester may be treated either neat or dissolved in a water insoluble organic solvent such as; aromatic solvents such as benzene, toluene, xylenes, ethyl benzene and the like; hydrocarbon solvents such as n-hexane, n-heptane, cyclohexane and the like; and ketones which will not react with bisulfite or dithionite, such as methyl isobutyl ketone and the like. Preferred solvents include benzene, toluene, and xylene. Treatment of neat ester is most preferred because it avoids the use of any solvent. Treatment of the ester can be either batchwise, that is, by adding the aqueous solution of bisulfite or dithionite to the ester, mixing with stirring or shaking, and allowing the mixture to separate, or continuous, that is, introducing the ester and aqueous solution into a mixer, continuously mixing them with stirring or shaking, feeding the mixture into a standing vessel where the layers separate, and withdrawing the ester and aqueous layers continuously from the vessel.

After separation front the ester, the aqueous solution may be discarded or it may be used to treat additional ester. That is, it may be recycled. It may also be combined with fresh aqueous solution prior to extraction of the ester. Recycling the aqueous solution will result in additional cost savings.

The presence of polymerization inhibitors such as, hydroquinone, hydroquinone monomethyl ether, methylene blue, phenothiazine, copper salicylate, copper dialkyldithiocarbamates, and the like, do not adversely affect the process.

The bisulfites and dithionites used include salts of alkali metals such as sodium bisulfite, sodium dithionite, potassium bisulfite, potassium dithionite, and cesium bisulfite and cesium dithionite as well as ammonium bisulfite and ammonium dithionite. The sodium, potassium and ammonium salts are preferred; bisulfite and sodium salts are most preferred. The salt concentration is not critical, aqueous bisulfite or dithionite solutions containing from about 0.1 to about 30 wt. %, of the salt, relative to the water, are preferred. The relative proportion of the aqueous solution to the ester or ester solution is also not critical. However, proportions of from about 5 to about 50 wt. % based on the weight of the ester or ester solution are preferred. Proportions of from about 5 to about 15 wt % are most preferred. The extraction temperature is also not critical, although it must remain below the boiling point of any solvent used. Temperatures front about ambient up to about 60° C. are preferred.

EXAMPLES

The following examples illustrate the present invention more specifically.

A stock butyl acrylate sample was obtained by acid-catalyzed esterification of acrylic acid with butyl alcohol. The acrylic acid was previously prepared from propylene by oxidation. Analysis of the stock sample showed that it contained 33 parts per million (ppm) of furfural, 6 ppm of protoanemonin, and 8 ppm of benzaldehyde. Subsamples of the stock solution were used in each of the following experiments:

Examples 1–4

Stock subsamples (44 g) were treated by adding about 5 g of an aqueous solution containing from 2 to 29 wt. % of sodium bisulfite to the subsample, thoroughly mixing the subsample and the solution, and then allowing the mixture to separate into an aqueous and a subsample layer. The total contact time was about 10 minutes. Each subsample layer was then analyzed for furfural, protoanemonin, and benzaldehyde content. The results of the analyses are in Table 1.

Example 5

Example 5 was treated in the same manner as Example 3 except that the subsample was extracted twice. The results of the analysis of this sample are also in Table 1.

TABLE 1

IMPURITY CONTENT BEFORE AND AFTER TREATMENT

| Example No. | wt. % NaHSO$_3$ | Furfural (ppm) | Protoanemonin (ppm) | Benzaldehyde (ppm) |
|---|---|---|---|---|
| Stock |  | 33 | 6 | 8 |
| 1 | 2 | 8 | 5 | 7 |
| 2 | 10 | 1 | 1 | 5 |
| 3 | 17 | 1 | ND | 4 |
| 4 | 29 | 1 | 4 | 5 |
| 5 | 2 × 17 | ND | 2 | 3 |

ND = not detected at a sensitivity of 0.5 ppm

Example 6

A stock subsample (44 g) was treated with about 5 g of an aqueous solution containing 17 wt. % of sodium dithionite. The mixture was shaken until thoroughly mixed, and then allowed to separate into an aqueous and a subsample layer. The total contact time was about 1.5 hours. The subsample layer was then analyzed for furfural, protoanemonin, and benzaldehyde content. The results of these analyses are in Table 2.

TABLE 2

IMPURITY CONTENT BEFORE AND AFTER TREATMENT

| Example No. | wt. % Na$_2$S$_2$O$_4$ | Furfural (ppm) | Protoanemonin (ppm) | Benzaldehyde (ppm) |
|---|---|---|---|---|
| Stock |  | 33 | 6 | 8 |
| 6 | 17 | 2 | 3 | 4 |

Examples 7–10

A stock solution of butyl acrylate was fortified with benzaldehyde and furfural to increase the effective levels of these impurities in the ester. A sample of this stock solution (50 g) was treated with about 50 g of an aqueous solution containing 5 wt% sodium dithionite (50 g) either 1, 2, or 3 times. In each treatment the two were shaken until well mixed and then allowed to separate into an aqueous and a subsample layer. The total contact time for each treatment was 5 minutes. The subsample layer was then analyzed for furfural, protoanemonin, and benzaldehyde content. The results of these analyses are summarized in Table 3.

TABLE 3

IMPURITY CONTENT BEFORE AND AFTER TREATMENT

| Example No. | wt. % Na$_2$S$_2$O$_4$ | Furfural (ppm) | Protoanemonin (ppm) | Benzaldehyde (ppm) |
|---|---|---|---|---|
| Stock |  | 159 | 2 | 138 |
| 7 | 1 × 5 | 6 | 3 | 95 |
| 8 | 2 × 5 | 1 | 2 | 46 |
| 9 | 3 × 5 | 0.1 | 2 | 37 |
| 10 | 3 × 5 | 1.7 | 0.8 | 43 |

These examples demonstrate the dramatic reduction in carbonyl containing impurities accomplished by the process of the present invention.

We claim:

1. A process for removing carbonyl-containing impurities from an $\alpha,\beta$-unsaturated carboxylic acid ester comprising the steps of:

a. effectively admixing the ester and an aqueous solution of a salt selected from bisulfites and dithionites; and b. separating the ester from the aqueous solution.

2. The process of claim 1 wherein the bisulfite salt is selected from sodium bisulfite, potassium bisulfite, cesium bisulfite, and ammonium bisulfite.

3. The process of claim 1 wherein the dithionite salt is selected from sodium dithionite, potassium dithionite, cesium dithionite, and ammonium dithionite.

4. The process of claim 3 wherein the dithionite salt is sodium dithionite.

5. The process of claim 2 wherein the bisulfite salt is sodium bisulfite.

6. The process of claim 1 wherein the $\alpha,\beta$-unsaturated carboxylic acid ester is selected from esters of $C_3$–$C_{10}$ carboxylic acids and $C_1$–$C_{10}$ alcohols.

7. The process of claim 1 wherein the $\alpha,\beta$-unsaturated carboxylic acid ester is selected from esters of $C_3$–$C_5$ carboxylic acids and $C_1$–$C_5$ alcohols.

8. The process of claim 7 wherein the $\alpha,\beta$-unsaturated carboxylic acid ester is selected from acrylic acid esters and methacrylic acid esters.

9. The process of claim 8 wherein the $\alpha,\beta$-unsaturated carboxylic acid ester is selected from methyl acrylate, butyl acrylate, ethyl acrylate, butyl methacrylate, and methyl methacrylate.

10. The process of claim 9 wherein the $\alpha,\beta$-unsaturated carboxylic acid ester is selected from butyl acrylate and ethyl acrylate.

11. The process of claim 1 wherein the ester is a water insoluble organic solvent solution of the $\alpha,\beta$-unsaturated carboxylic acid ester.

12. The process of claim 1 further comprising the step of recycling the aqueous solution after separating the ester from the aqueous solution.

* * * * *